(12) United States Patent
Kang

(10) Patent No.: US 11,656,214 B2
(45) Date of Patent: May 23, 2023

(54) QUANTIFYING METHOD OF UNCERTAINTY OF MEASURED VALUE BY CLOSE MATCH SPAN CALIBRATION OF MEASURING SENSOR AND THE APPARATUS USING THE SAME

(71) Applicant: KOREA RESEARCH INSTITUTE OF STANDARDS AND SCIENCE, Daejeon (KR)

(72) Inventor: Nam Goo Kang, Daejeon (KR)

(*) Notice: Subject to any disclaimer, the term of this patent is extended or adjusted under 35 U.S.C. 154(b) by 0 days.

(21) Appl. No.: 17/348,804

(22) Filed: Jun. 16, 2021

(65) Prior Publication Data
US 2022/0074904 A1    Mar. 10, 2022

(51) Int. Cl.
*G01N 33/00*    (2006.01)
(52) U.S. Cl.
CPC .................... *G01N 33/007* (2013.01)
(58) Field of Classification Search
CPC .................................................... G01N 33/007
See application file for complete search history.

(56) References Cited

PUBLICATIONS

Farrance ett al., "Uncertainty of Measurement: A Review of the Rules for Calculating Uncertainty Components through Functional Relationships", Clin Biochem Rev vol. 33 May 2012 (Year: 2012).*

* cited by examiner

Primary Examiner — Regis J Betsch

(57) ABSTRACT

Disclosed herein is a quantifying method of uncertainty of measured value by close match span calibration of measuring sensor comprising a step of:
a quantifying using below equation I.

$$u_c(x_{bag}) \simeq \sqrt{\left[\frac{1}{f_{cyl}}u(R_{bag})\right]^2 + \left[\frac{1}{f_{cyl}}u(R_{cyl})\right]^2 + u^2(x_{cyl})} \quad (I)$$

wherein, $u_c$ is a combined standard uncertainty, $X_{bag}$ is a measured value of a test, $x_{cyl}$ is standard value, $f_{cyl}$ is standard response factor (sensitivity coefficient), $R_{bag}$ is a signal value of a test, represents $x_{bag} \cdot f_{bag}$, $R_{cyl}$ represents $x_{cyl} \cdot f_{cyl}$, and u is standard uncertainty.

4 Claims, 1 Drawing Sheet

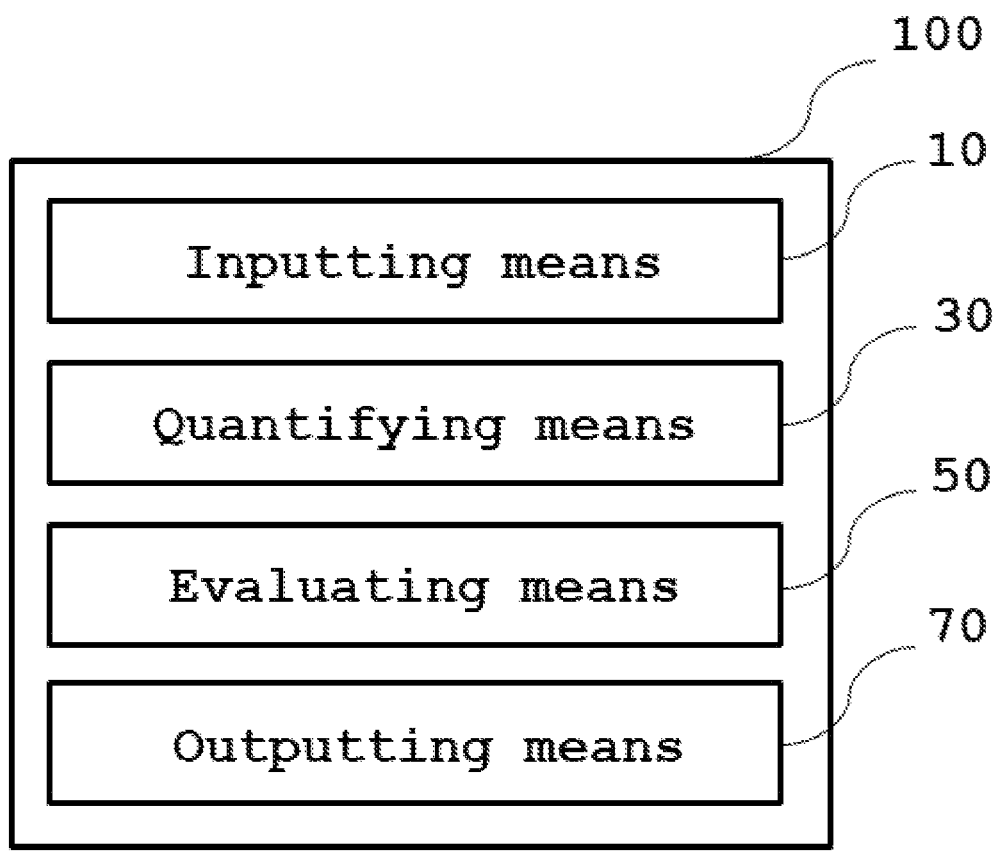

QUANTIFYING METHOD OF UNCERTAINTY OF MEASURED VALUE BY CLOSE MATCH SPAN CALIBRATION OF MEASURING SENSOR AND THE APPARATUS USING THE SAME

CROSS-REFERENCE TO RELATED APPLICATIONS

This application claims priority to Korean Patent Application 10-2020-0113420, filed on Sep. 4, 2020, the entire disclosure of which is incorporated herein by reference.

BACKGROUND

Field

Embodiments of the present invention relate to quantifying method of uncertainty of measured value by close match span calibration and the apparatus, and, more particularly, to quantifying method of uncertainty of measured value by close match span calibration of measuring sensor and the apparatus to provide a method and an apparatus to derive a generalized equation to quantify the measurement uncertainty using the OPCM calibration, quantifying relative contributions of relevant uncertainty sources.

Description of the Related Art

The uncertainty of measured value (ex, voltage, current, resistance) using sensors are quantitative characteristics of the quality or the credibility of said sensors.

Up to now, there has been 'offset and span calibration' method for calibration method used to correct said sensors. Said method uses linear transfer function which is quantitatively related function between measured values and sensor output signals, and needs the process of correcting offset regarding y-axis to zero. This calibration method is called one-point through origin (OPTO)

The one-point through-origin (OPTO) calibration is being frequently used for quantification of analyte in a sample where a calibration line using standards must pass through a zero response in instrumentation. This requirement is not valid in many cases.

Recently one-point close-match (OPCM) calibration is briefly introduced to an international standard. (ISO 12963: 2017).

The OPCM calibration model has an advantage over the OPTO calibration in that the former does not require the assumption of linearity through origin.

However, information is basically lacking on how to derive the uncertainty estimation model based on the OPCM calibration and how to quantitatively assess the influence of relevant uncertainty sources. Information with regard to these two has not been reported to date.

Therefore, under these circumstances there are some problems of not being able to optimize managements because it is difficult to determine the priority among managements regarding relevant uncertainty sources.

SUMMARY

Therefore, the present invention has been made in view of the above problems, and it is an object of the present invention to provide a method and an apparatus to derive a generalized equation to quantify the measurement uncertainty using the OPCM calibration, quantifying relative contributions of relevant uncertainty sources.

In accordance with a first aspect of present invention, the above objects can be accomplished by following means;

A quantifying method of uncertainty of measured value by close match span calibration of measuring sensor using below equation I.

$$u_c(x_{bag}) \simeq \sqrt{\left[\frac{1}{f_{cyl}}u(R_{bag})\right]^2 + \left[\frac{1}{f_{cyl}}u(R_{cyl})\right]^2 + u^2(x_{cyl})} \quad (I)$$

wherein, $u_c$ is a combined standard uncertainty, $X_{bag}$ is a measured value of a test, $x_{cyl}$ is standard value, $f_{cyl}$ is standard response factor (sensitivity coefficient), $R_{bag}$ is a signal value of a test, represents $x_{bag} \cdot f_{bag}$, $R_{cyl}$ represents $x_{cyl} \cdot f_{cyl}$, and u is standard uncertainty.

In accordance with the first aspect of the present invention, the above and other objects can be accomplished by quantifying relative contributions of relevant uncertainty sources using below equation II.

$$h(R_{bag}) = \frac{\left[\frac{1}{f_{cyl}}u(R_{bag})\right]^2}{u_c^2(x_{bag})}; \quad (II)$$

$$h(R_{cyl}) = \frac{\left[\frac{1}{f_{cyl}}u(R_{cyl})\right]^2}{u_c^2(x_{bag})};$$

$$h(x_{cyl}) = \frac{u^2(x_{cyl})}{u_c^2(x_{bag})}$$

In accordance with the first aspect of the present invention, preferably the measuring sensor is gas sensor.

In accordance with a second aspect of the present invention, the above objects can be accomplished by a quantifying apparatus of uncertainty of measured value by close match span calibration of measuring sensor using below equation I.

$$u_c(x_{bag}) \simeq \sqrt{\left[\frac{1}{f_{cyl}}u(R_{bag})\right]^2 + \left[\frac{1}{f_{cyl}}u(R_{cyl})\right]^2 + u^2(x_{cyl})} \quad (I)$$

wherein, $u_c$ is a combined standard uncertainty, $X_{bag}$ is a measured value of a test, $x_{cyl}$ is standard value, $f_{cyl}$ is standard response factor (sensitivity coefficient), $R_{bag}$ is a signal value of a test, represents $x_{bag} \cdot f_{bag}$, $R_{cyl}$ represents $x_{cyl} \cdot f_{cyl}$, and u is standard uncertainty.

In accordance with the second aspect of the present invention, the above and other objects can be accomplished by quantifying relative contributions of relevant uncertainty sources using below equation II.

$$h(R_{bag}) = \frac{\left[\frac{1}{f_{cyl}}u(R_{bag})\right]^2}{u_c^2(x_{bag})}; \quad (II)$$

$$h(R_{cyl}) = \frac{\left[\frac{1}{f_{cyl}}u(R_{cyl})\right]^2}{u_c^2(x_{bag})};$$

-continued $$h(x_{cyl}) = \frac{u^2(x_{cyl})}{u_c^2(x_{bag})}$$

In accordance with the second aspect of the present invention, preferably the measuring sensor is gas sensor.

In accordance with a third aspect of the present invention, the above objects can be accomplished by computer-readable recording medium recording program to implement the method.

BRIEF DESCRIPTION OF THE DRAWINGS

The above and other objects, features and other advantages of the present invention will be more clearly understood from the following detailed description taken in conjunction with the accompanying drawings, in which:

FIG. 1 is a block diagram illustrating the construction of quantifying apparatus of uncertainty of measured value by close match span calibration.

DETAILED DESCRIPTION OF EMBODIMENTS

Hereinafter, various embodiments according to the present invention will be described in detail with reference to the accompanying drawings. The detailed description to be described below with reference to the accompanying drawings is intended to illustrate exemplary embodiments of the invention and is not intended to represent the only embodiment in which the invention may be executed. The following detailed description includes specific details in order to provide a complete understanding of the present invention. However, those skilled in the art will appreciate that the present invention may be executed without these specific details.

In some cases, well-known structures and devices will not be described or will be illustrated in a block diagram form centering on core functions of each structure and apparatus, to avoid obscuring concepts of the present invention.

In the specification, when the explanatory phrase a part "comprises or includes" a component is used, this means that the part may further include the component without excluding other components, so long as special explanation is not given. Further, the term " . . . unit" described in the specification means a unit for processing at least one function or operation. In addition, as used herein the context for describing the present invention (particularly, in the context of the following claims), the singular forms "a," "an," "one" and "the" are intended to include the plural forms as well, unless the context clearly indicates otherwise in the specification or is clearly limited by the context.

In description of exemplary embodiments of the present invention, the publicly known functions and configurations that are judged to be able to make the purport of the present invention unnecessarily obscure will not be described in detail.

Further, wordings to be described below are defined in consideration of the functions of the present invention, and may differ depending on the intentions of a user or an operator or custom. Accordingly, such wordings should be defined on the basis of the contents of the overall specification.

Hereinafter, exemplary embodiments of the present invention will be described with reference to the accompanying drawings.

Embodiments of the present invention of quantifying method of uncertainty of measured value by close match span calibration of measuring sensor concern calibrating method, and several sensors such as gas sensor, pressure sensor, current sensor, etc.

Embodiments of the present invention provide means to quantify and calculate combined standard uncertainty regarding measured values using OPCM calibration, and quantify relative contributions of relevant uncertainty sources regarding said combined standard uncertainty.

According to exemplary embodiments of the present invention, preferably, above means automatically give input values mechanically, or is given input values manually using below equation I to calculate combined standard uncertainty automatically.

$$u_c(x_{bag}) \simeq \sqrt{\left[\frac{1}{f_{cyl}}u(R_{bag})\right]^2 + \left[\frac{1}{f_{cyl}}u(R_{cyl})\right]^2 + u^2(x_{cyl})} \quad (I)$$

wherein, $u_c$ is a combined standard uncertainty, $X_{bag}$ is measured value of a test, $x_{cyl}$ is standard value, $f_{cyl}$ is standard response factor (sensitivity coefficient), $R_{bag}$ is signal value of a test, represents $X_{bag} \cdot f_{bag}$, $R_{cyl}$ represents $x_{cyl} \cdot f_{cyl}$, and u is standard uncertainty.

Also, according to exemplary embodiments of the present invention, it is possible to calculate relative contributions of relevant uncertainty sources regarding combined standard uncertainty. Using this result, it is possible to calculate relative contributions of relevant uncertainty sources to contribute to the combined standard uncertainty regarding measured results using OPCM calibration.

$$h(R_{bag}) = \frac{\left[\frac{1}{f_{cyl}}u(R_{bag})\right]^2}{u_c^2(x_{bag})}; \quad (II)$$

$$h(R_{cyl}) = \frac{\left[\frac{1}{f_{cyl}}u(R_{cyl})\right]^2}{u_c^2(x_{bag})};$$

$$h(x_{cyl}) = \frac{u^2(x_{cyl})}{u_c^2(x_{bag})}$$

As described above, if we get relative contributions of relevant uncertainty sources $h(R_{bag})$, $h(R_{cyl})$, and $h(X_{cyl})$ using equation II, it is possible to use as useful information to determine the priority among managements regarding relevant uncertainty sources.

Hereinafter, exemplary embodiments of the present invention will be described in detail regarding the process to derive related function for evaluation model of combined standard uncertainty, and calculation of relative contributions of relevant uncertainty sources to contribute to the combined standard uncertainty. In these embodiments, the measuring sensor is gas sensor, and the gas is methane as one of green house gas species A requirement for the OPCM calibration is that, for example, the amount fraction of methane, a greenhouse gas species, in a calibration cylinder must be very close to that in the sampling bag:

$$X_{bag} = (X_{bag} - x_{cyl}) + X_{cyl} \quad (1)$$

The response factors (i.e., instrument sensitivity) of methane in the sampling bag and the calibration cylinder using a typical instrumentation (e.g., GC-FID) are defined as:

$$f_{bag} = \frac{R_{bag}}{x_{bag}}; \quad (2)$$

$$f_{cyl} = \frac{R_{cyl}}{x_{cyl}}$$

The methane fractions in the sampling bag and the calibration gas cylinder are expressed as a function of the response factor f (i.e., calibration function), respectively.

$$x_{bag} = \frac{R_{bag}}{f_{bag}}; \quad (3)$$

$$x_{cyl} = \frac{R_{cyl}}{f_{cyl}}$$

This is applied to the right-hand side of Equation (1), which yields:

$$x_{bag} = \left(\frac{R_{bag}}{f_{bag}} - \frac{R_{cyl}}{f_{cyl}}\right) + x_{cyl} \quad (4)$$

The response factor f of the instrument should be constant to the same component methane under the close-match conditions regardless of the gas containers used:

$$f_{bag} = f_{cyl} \quad (5)$$

Now Equation (4) can be expressed as:

$$x_{bag} = \frac{1}{f_{cyl}}(R_{bag} - R_{cyl}) + x_{cyl} \quad (6)$$

Therefore the combined standard uncertainty of the methane fraction in the sampling bag:

$$u_c(x_{bag}) = u\left[\frac{1}{f_{cyl}}(R_{bag} - R_{cyl}) + x_{cyl}\right] \quad (7)$$

Squaring both sides yields:

$$u_c^2(x_{bag}) = u^2\left[\frac{1}{f_{cyl}}(R_{bag} - R_{cyl}) + x_{cyl}\right] \quad (8)$$

The law of uncertainty propagation with a 1st order Taylor series is applied to Equation (8) in order to derive the square of the combined standard uncertainty of methane in a sampling bag:

$$u_c^2(x_{bag}) = u^2\left[\frac{1}{f_{cyl}}(R_{bag} - R_{cyl})\right] + u^2(x_{cyl}) \quad (9)$$

where $u(x_{cyl})$ is the combined standard uncertainty of the methane fraction in the calibration cylinder.

Multiplying $$\left[\frac{1}{f_{cyl}}(R_{bag} - R_{cyl})\right]^2,$$

and dividing by $$\left[\frac{1}{f_{cyl}}(R_{bag} - R_{cyl})\right]^2$$

for the righthand side of Equation (9) yields:

$$u_c^2(x_{bag}) = \left[\frac{1}{f}(R_{bag} - R_{cyl})\right]^2 \frac{u^2\left[\frac{1}{f_{cyl}}(R_{bag} - R_{cyl})\right]}{\left[\frac{1}{f_{cyl}}(R_{bag} - R_{cyl})\right]^2} + u^2(x_{cyl}) \quad (10)$$

$$u_c^2(x_{bag}) = \left[\frac{1}{f_{cyl}}(R_{bag} - R_{cyl})\right]^2 u_{rel}^2\left[\frac{1}{f_{cyl}}(R_{bag} - R_{cyl})\right] + u^2(x_{cyl}) \quad (11)$$

where, $$u_{rel}^2\left[\frac{1}{f_{cyl}}(R_{bag} - R_{cyl})\right] = \left[u_{rel}^2(f) + u_{rel}^2(R_{bag} - R_{cyl})\right] \quad (12)$$

Now using Equation (12), Equation (11) can be expressed as:

$$u_c^2(x_{bag}) = \left[\frac{1}{f_{cyl}}(R_{bag} - R_{cyl})\right]^2 \left[u_{rel}^2(f) + u_{rel}^2(R_{bag} - R_{cyl})\right] + u^2(x_{cyl}) \quad (13)$$

$$u_c^2(x_{bag}) = \left[\frac{1}{f_{cyl}}(R_{bag} - R_{cyl})\right]^2 \left[\frac{y^2(f_{cyl})}{f_{cyl}^2} + \frac{u^2(R_{bag} - R_{cyl})}{(R_{bag} - R_{cyl})^2}\right] + u^2(x_{cyl}) \quad (14)$$

Applying the law of uncertainty propagation for addition or subtraction to $u^2(R_{bag} - R_{cyl})$, yields:

$$u^2(R_{bag} - R_{cyl}) = u^2(R_{bag}) + u^2(R_{cyl}) \quad (15)$$

Thus Equation (14) would be:

$$u_c^2(x_{bag}) = \quad (16)$$

$$\left(\frac{1}{f_{cyl}}\right)^2 (R_{bag} - R_{cyl})^2 \left[\frac{u^2(f_{cyl})}{f_{cyl}^2} + \frac{u^2(R_{bag}) + u^2(R_{cyl})}{(R_{bag} - R_{cyl})^2}\right] + u^2(x_{cyl})$$

$$u_c^2(x_{bag}) = \frac{u_{(f)}^2}{f_{cyl}^4}(R_{bag} - R_{cyl})^2 + \frac{1}{f_{cyl}^2}\left[u^2(R_{bag}) + u^2(R_{cyl})\right] + u^2(x_{cyl}) \quad (17)$$

$$u_c(x_{bag}) = \quad (18)$$

$$\sqrt{\frac{u^2(f_{cyl})}{f_{cyl}^4}(R_{bag} - R_{cyl})^2 + \frac{1}{f_{cyl}^2}\{u^2(R_{bag}) + u^2(R_{cyl})\} + u^2(x_{cyl})}$$

$$u_c(x_{bag}) = \quad (19)$$

$$\sqrt{\left[\frac{(R_{bag} - R_{cyl})}{f_{cyl}^2}u(f_{cyl})\right]^2 + \left[\frac{1}{f_{cyl}}u(R_{bag})\right]^2 + \left[\frac{1}{f_{cyl}}u(R_{cyl})\right]^2 + u^2(x_{cyl})}$$

where, $u(f_{cyl}) = u\left(\frac{R_{cyl}}{x_{cyl}}\right)$ (20)

Applying the law of uncertainty propagation for multiplication or division yields:

$$\left[\frac{u(f_{cyl})}{f_{cyl}}\right]^2 = \left[\frac{u(R_{cyl})}{R_{cyl}}\right]^2 + \left[\frac{u(x_{cyl})}{x_{cyl}}\right]^2 \quad (21)$$

Using Equation (21), Equation (19) can be expressed as:

$$u_c(x_{bag}) = \sqrt{\left[\frac{(R_{bag}-R_{cyl})}{f_{cyl}}\sqrt{\left[\frac{u^2(R_{cyl})}{R_{cyl}^2} + \frac{u^2(x_{cyl})}{x_{cyl}^2}\right]}\right]^2 + \left[\frac{1}{f_{cyl}}u(R_{bag})\right]^2 + \left[\frac{1}{f_{cyl}}u(R_{cyl})\right]^2 + u^2(x_{cyl})} \quad (22)$$

Now that the requirement must be met (i.e., is very near to):

$$\left[\frac{(R_{bag}-R_{cyl})}{f_{cyl}}\sqrt{\left[\frac{u^2(R_{cyl})}{R_{cyl}^2} + \frac{u^2(x_{cyl})}{x_{cyl}^2}\right]}\right]^2 \ll \left[\frac{1}{f_{cyl}}u(R_{bag})\right]^2 + \left[\frac{1}{f_{cyl}}u(R_{cyl})\right]^2 + u^2(x_{cyl}) \quad (23)$$

As a consequence, a simplified equation in terms of variance is derived:

$$u_c(x_{bag}) \simeq \sqrt{\left[\frac{1}{f_{cyl}}u(R_{bag})\right]^2 + \left[\frac{1}{f_{cyl}}u(R_{cyl})\right]^2 + u^2(x_{cyl})} \quad (I)$$

wherein, $u_c$ is a combined standard uncertainty, $X_{bag}$ is a measured value of a test, $x_{cyl}$ is standard value, $f_{cyl}$ is standard response factor (sensitivity coefficient), $R_{bag}$ is a signal value of a test, represents $x_{bag} \cdot f_{bag}$, $R_{cyl}$ represents $x_{cyl} \cdot f_{cyl}$, and u is standard uncertainty.

The relative contribution (%) of each uncertainty source on the combined standard uncertainty of is estimated:

$$h(R_{bag}) = \frac{\left[\frac{1}{f_{cyl}}u(R_{bag})\right]^2}{u_c^2(x_{bag})};$$

$$h(R_{cyl}) = \frac{\left[\frac{1}{f_{cyl}}u(R_{cyl})\right]^2}{u_c^2(x_{bag})};$$

$$h(x_{cyl}) = \frac{u^2(x_{cyl})}{u_c^2(x_{bag})} \quad (II)$$

In addition, exemplary embodiments of the present invention, as shown in FIG. 1, provide an apparatus 100 for quantifying uncertainty of measured value by close match span calibration of measuring sensor comprising a means for quantifying uncertainty 30, and a means for assaying relative contributions of relevant uncertainty sources regarding said uncertainty 50.

More specifically, the apparatus 100 comprises an inputting means 10 which inputs data of $f_{cyl}$, $u(R_{bag})$, $u(R_{cyl})$, and $u(x_{cyl})$, a quantifying means 30 which calculates combined standard uncertainty $u_c(x_{bag})$ using equation I after receiving said data, an evaluating means 50 for evaluating relative contributions of relevant uncertainty sources regarding said uncertainty using equation II, an outputting means 70 which outputs the results calculated by an evaluating means 50.

$$u_c(x_{bag}) \simeq \sqrt{\left[\frac{1}{f_{cyl}}u(R_{bag})\right]^2 + \left[\frac{1}{f_{cyl}}u(R_{cyl})\right]^2 + u^2(x_{cyl})} \quad (I)$$

wherein, $u_c$ is a combined standard uncertainty, $X_{bag}$ is a measured value of a test, $x_c y_j$ is standard value, $f_{cyl}$ is standard response factor (sensitivity coefficient), $R_{bag}$ is a signal value of a test, represents $x_{bag} \cdot f_{bag}$, $R_{cyl}$ represents $x_{cyl} \cdot f_{cyl}$, and u is standard uncertainty.

$$h(R_{bag}) = \frac{\left[\frac{1}{f_{cyl}}u(R_{bag})\right]^2}{u_c^2(x_{bag})};$$

$$h(R_{cyl}) = \frac{\left[\frac{1}{f_{cyl}}u(R_{cyl})\right]^2}{u_c^2(x_{bag})};$$

$$h(x_{cyl}) = \frac{u^2(x_{cyl})}{u_c^2(x_{bag})} \quad (II)$$

The quantifying means 30 and the evaluating means 50 can be implemented to computer-readable program, optionally can be implemented using firmware or hardware, and Micom can be used to calculate equation I and equation II.

According to exemplary embodiments of the present invention, a simplified equation for the uncertainty estimation model of the OPCM calibration is newly developed using the law of uncertainty propagation (1st-order Taylor series model). This model can assess the relative contributions of relevant uncertainty sources.

An important application of this uncertainty model needs to be highlighted: an analyst can determine whether observed biases of manual or automated gas sampling methods used in the GC-FID are statistically significant. This uncertainty model would be widely applicable to one-point calibration in analytical sciences (e.g., chemical analysis) where it is impossible in reality to assume linearity through origin.

A limited number of possible embodiments for the present teachings have been presented above for illustrative purposes. Those of ordinary skill in the art will appreciate that various modifications, additions, and substitutions are possible. While this patent document contains many specifics, these should not be construed as limitations on the scope of the present teachings or of what may be claimed, but rather as descriptions of features that may be specific to particular embodiments. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A quantifying method of uncertainty of a measured value by close match span calibration of a gas sensor comprising the steps of:

taking the measured value from the gas sensor; and quantifying the uncertainty of the measured value, using below equation I, $$u_c(x_{bag}) \simeq \sqrt{\left[\frac{1}{f_{cyl}}u(R_{bag})\right]^2 + \left[\frac{1}{f_{cyl}}u(R_{cyl})\right]^2 + u^2(x_{cyl})} \quad (I)$$

wherein, $u_c$ is a combined standard uncertainty, $X_{bag}$ is a measured value of a test of a sampling bag, taken from the gas sensor, $x_{cyl}$ is a standard value, $f_{bag}$ is a response factor of the test of the sampling bag, $f_{cyl}$ is a standard response factor (a sensitivity coefficient), $R_{bag}$ is a signal value of a test, which is $x_{bag} \cdot f_{bag}$, $R_{cyl}$ is a standard signal value of the test, which is $x_{cyl} \cdot f_{cyl}$, and u is standard uncertainty.

2. The quantifying method according to claim 1, further comprising the step of:

quantifying relative contributions of relevant uncertainty sources using below equation II $$h(R_{bag}) = \frac{\left[\frac{1}{f_{cyl}}u(R_{bag})\right]^2}{u_c^2(x_{bag})}; h(R_{cyl}) = \frac{\left[\frac{1}{f_{cyl}}u(R_{cyl})\right]^2}{u_c^2(x_{bag})}; h(x_{cyl}) = \frac{u^2(x_{cyl})}{u_c^2(x_{bag})} \quad (II)$$

3. A quantifying apparatus of uncertainty of a measured value by close match span calibration of a gas sensor, wherein the quantifying apparatus is configured to take the measured value from the gas sensor and to use below equation I, $$u_c(x_{bag}) \simeq \sqrt{\left[\frac{1}{f_{cyl}}u(R_{bag})\right]^2 + \left[\frac{1}{f_{cyl}}u(R_{cyl})\right]^2 + u^2(x_{cyl})} \quad (I)$$

wherein, $u_c$ is a combined standard uncertainty, $X_{bag}$ is a measured value of a test of a sampling bag, taken from the gas sensor, $x_{cyl}$ is a standard value, $f_{cyl}$ is a standard response factor (a sensitivity coefficient), $R_{bag}$ is a signal value of a test, which is $x_{bag} \cdot f_{bag}$, $R_{cyl}$ is a standard signal value of the test, which is $x_{cyl} \cdot f_{cyl}$, and u is standard uncertainty.

4. The quantifying apparatus according to claim 3, further comprising:

quantifying means of relative contributions of relevant uncertainty sources using below equation II $$h(R_{bag}) = \frac{\left[\frac{1}{f_{cyl}}u(R_{bag})\right]^2}{u_c^2(x_{bag})}; h(R_{cyl}) = \frac{\left[\frac{1}{f_{cyl}}u(R_{cyl})\right]^2}{u_c^2(x_{bag})}; h(x_{cyl}) = \frac{u^2(x_{cyl})}{u_c^2(x_{bag})} \quad (II)$$

* * * * *